(12) United States Patent
Sinton et al.

(10) Patent No.: US 12,357,991 B2
(45) Date of Patent: Jul. 15, 2025

(54) SPERM SELECTION DEVICE, KIT, AND METHODS

(71) Applicants: David Sinton, Toronto (CA); Jason Riordon, Toronto (CA); Mohammad Simchi, Toronto (CA)

(72) Inventors: David Sinton, Toronto (CA); Jason Riordon, Toronto (CA); Mohammad Simchi, Toronto (CA)

( * ) Notice: Subject to any disclaimer, the term of this patent is extended or adjusted under 35 U.S.C. 154(b) by 1119 days.

(21) Appl. No.: 17/238,291

(22) Filed: Apr. 23, 2021

(65) Prior Publication Data

US 2021/0354142 A1 Nov. 18, 2021

Related U.S. Application Data

(60) Provisional application No. 63/025,308, filed on May 15, 2020.

(51) Int. Cl.
| | |
|---|---|
| *C12N 5/071* | (2010.01) |
| *B01L 3/00* | (2006.01) |
| *B29C 53/56* | (2006.01) |
| *B33Y 80/00* | (2015.01) |
| *C12N 5/076* | (2010.01) |
| *G01N 1/40* | (2006.01) |
| *G01N 33/50* | (2006.01) |
| *B29L 31/00* | (2006.01) |

(52) U.S. Cl.
CPC ... *B01L 3/502761* (2013.01); *B01L 3/502707* (2013.01); *B29C 53/56* (2013.01); *B33Y 80/00* (2014.12); *C12N 5/061* (2013.01); *C12N 5/0612* (2013.01); *G01N 1/4077* (2013.01); *G01N 33/5005* (2013.01); *B01L 2200/0652* (2013.01); *B29L 2031/753* (2013.01)

(58) Field of Classification Search
CPC .......... C12N 5/0612; B01L 2200/0652; C12M 47/04
See application file for complete search history.

(56) References Cited

U.S. PATENT DOCUMENTS

| | | |
|---|---|---|
| 4,759,344 A | 7/1988 | Wang |
| 5,427,946 A | 6/1995 | Kricka et al. |
| 5,686,302 A | 11/1997 | Zech |
| 5,744,366 A | 4/1998 | Kricka et al. |
| 5,866,354 A | 2/1999 | Froman |
| 5,908,380 A | 6/1999 | Zavos et al. |
| 6,357,596 B1 | 3/2002 | Weichselbaum et al. |
| 6,783,928 B2 | 8/2004 | Hvichia et al. |
| 6,929,945 B2 | 8/2005 | Aravanis et al. |
| 7,108,966 B2 | 9/2006 | Aravanis et al. |
| 7,179,641 B2 | 2/2007 | Brickwood |

(Continued)

FOREIGN PATENT DOCUMENTS

| | | | |
|---|---|---|---|
| WO | 2004108011 A1 | 12/2004 | |
| WO | WO-2015104797 A1 * | 7/2015 | ............ C12M 47/04 |

*Primary Examiner* — Jonathan M Hurst
(74) *Attorney, Agent, or Firm* — ABM INTELLECTUAL PROPERTY INC.

(57) ABSTRACT

A device for selecting sperm includes a stack of a plurality of layers of a material. The stack has an inlet end and an outlet end. Each layer of the material includes a plurality of sperm selection microchannels. Each sperm selection microchannel has a respective microchannel inlet at the inlet end of the stack and extends to a respective microchannel outlet at the outlet end of the stack.

18 Claims, 16 Drawing Sheets

(56) References Cited

U.S. PATENT DOCUMENTS

| | | |
|---|---|---|
| 7,355,696 B2 | 4/2008 | Mueth et al. |
| 9,663,755 B2 | 5/2017 | Nosrati et al. |
| 10,422,737 B2 | 9/2019 | Demirci et al. |
| 10,450,545 B2 | 10/2019 | Pan et al. |
| 10,852,298 B2 | 12/2020 | Nosrati et al. |
| 2003/0096395 A1 | 5/2003 | Brickwood |
| 2004/0219507 A1 | 11/2004 | Abed |
| 2004/0234941 A1 | 11/2004 | Abed |
| 2006/0110821 A1 | 5/2006 | Brickwood |
| 2006/0144707 A1 | 7/2006 | Landers et al. |
| 2010/0291535 A1 | 11/2010 | Yao et al. |
| 2011/0061472 A1 | 3/2011 | Wo et al. |
| 2013/0029312 A1 | 1/2013 | Johnston |
| 2013/0164838 A1* | 6/2013 | Zech .................... C12N 5/0612 435/325 |
| 2019/0316084 A1 | 10/2019 | Demirci et al. |
| 2020/0069296 A1 | 3/2020 | Tarlan et al. |

\* cited by examiner

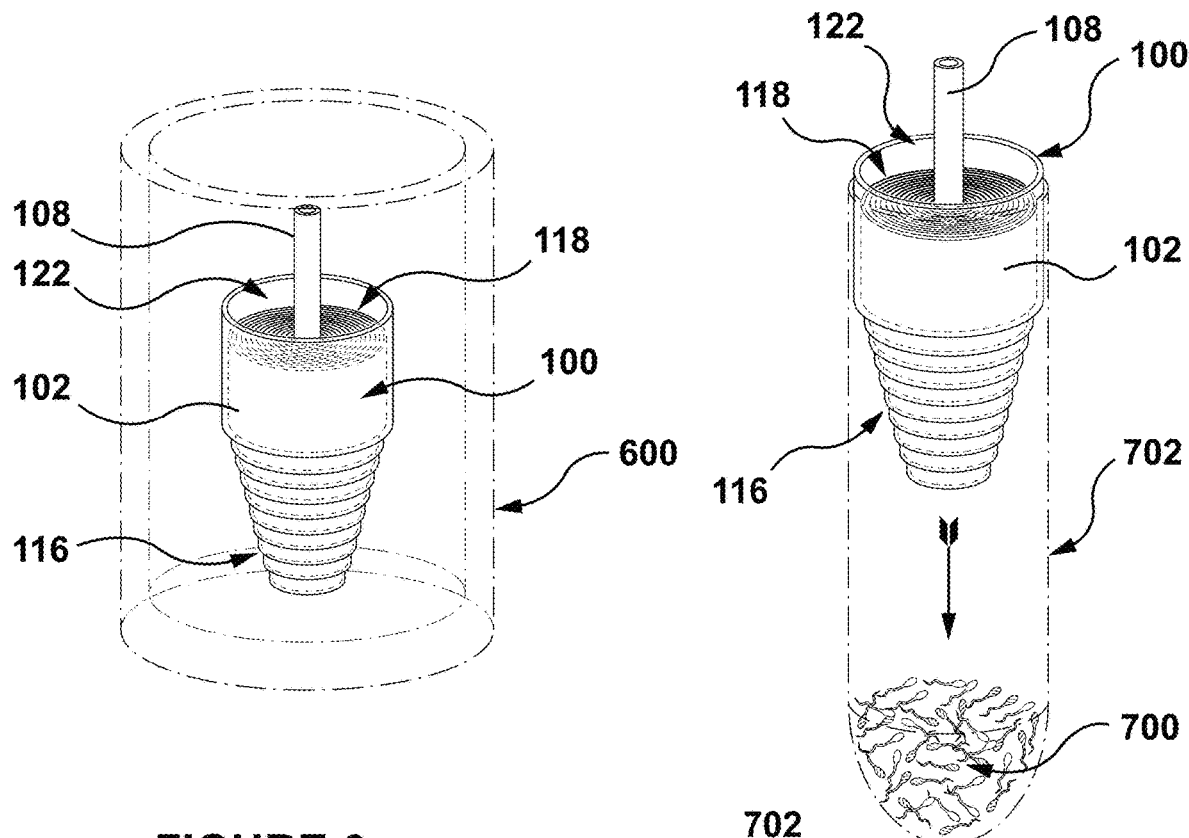
FIGURE 6
FIGURE 7
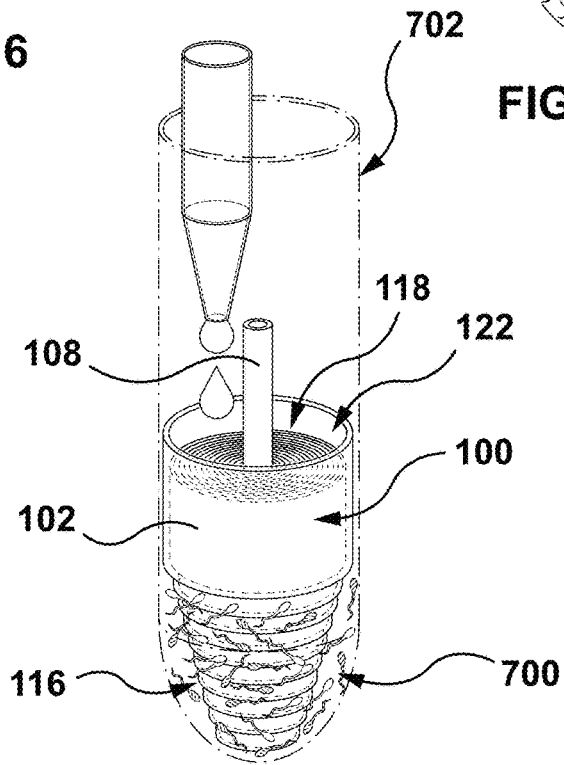
FIGURE 8

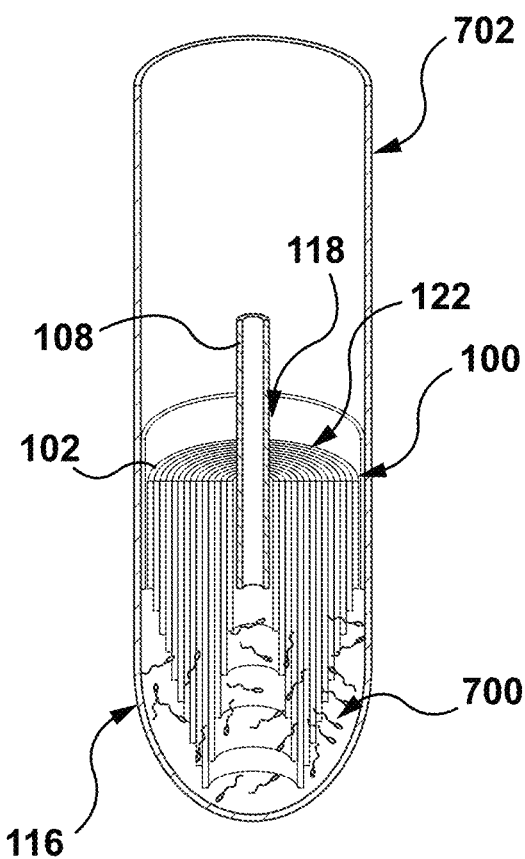
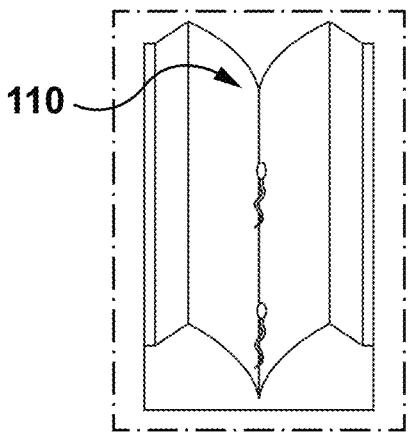
FIGURE 11B
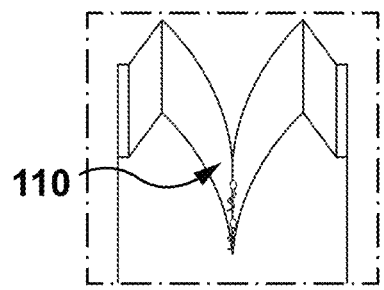
FIGURE 11C
FIGURE 11A
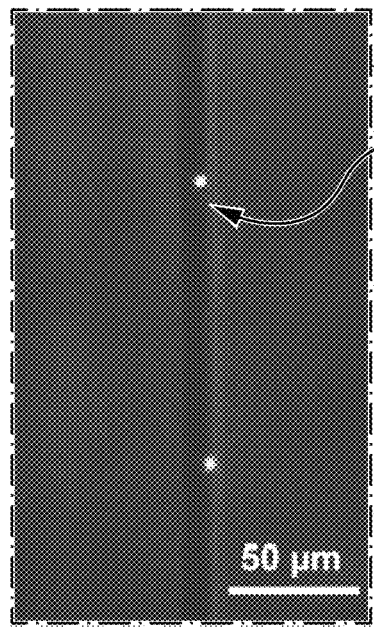
FIGURE 11D
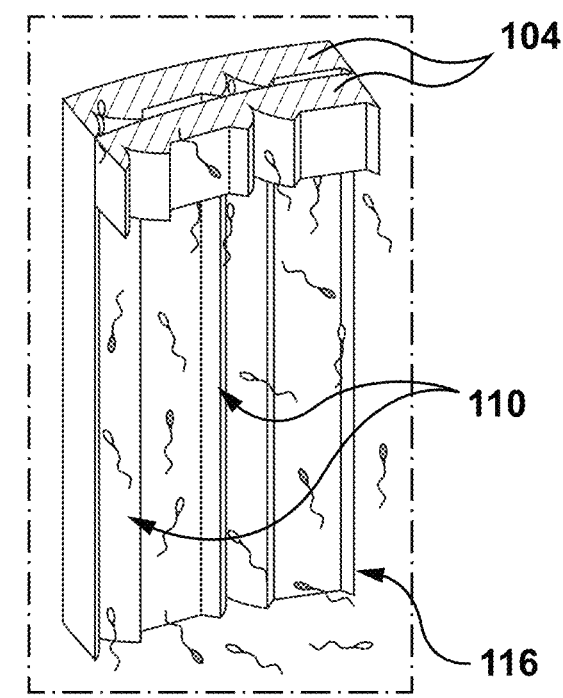
FIGURE 11E

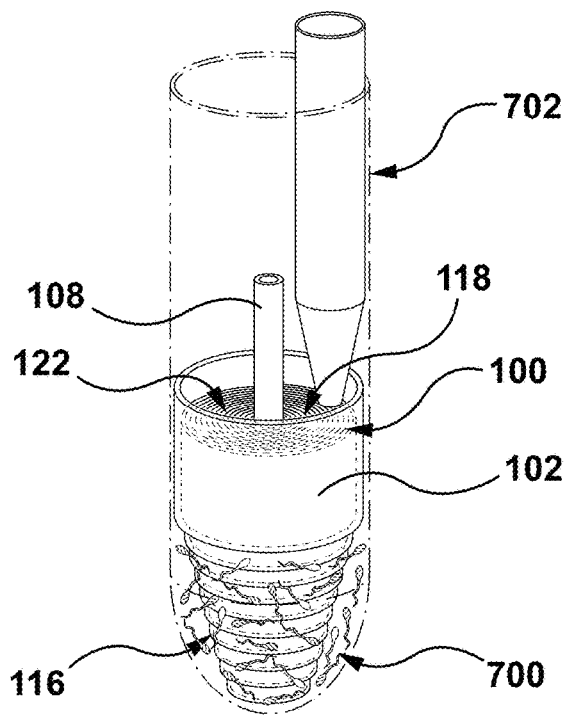
FIGURE 12
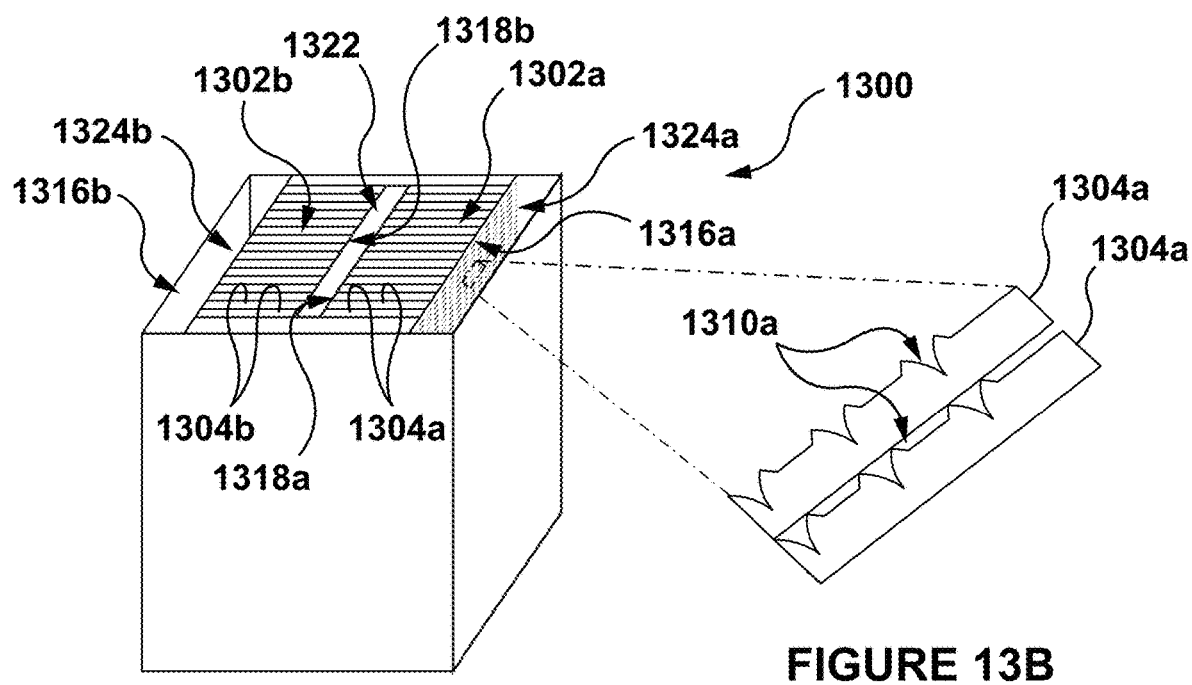
FIGURE 13A
FIGURE 13B

SPERM SELECTION DEVICE, KIT, AND METHODS

CROSS REFERENCES TO RELATED APPLICATIONS

This application claims the benefit of U.S. provisional patent application No. 63/025,308 filed on May 15, 2020, which is incorporated herein by reference in its entirety.

FIELD

This document relates to sperm selection, such as the selection of high-quality sperm for assisted reproduction. More specifically, this document relates to devices for selecting sperm, kits containing such devices, methods for fabricating such devices, and methods for selecting sperm.

BACKGROUND

U.S. patent application publication no. 2019/0316084A1 (Demirci et al.) discloses a method for sorting motile cells that includes introducing an initial population of motile cells into an inlet port of a microfluidic channel, where the initial population of motile cells has a first average motility, incubating the population of motile cells in the microfluidic channel, and collecting a sorted population of motile cells at an outlet port of the microfluidic channel. The sorted population of motile cells has a second average motility higher than the first average motility.

SUMMARY

The following summary is intended to introduce the reader to various aspects of the detailed description, but not to define or delimit any invention.

Devices for selecting sperm are disclosed. According to some aspects, a device for selecting sperm includes a stack of a plurality of layers of a material. The stack has an inlet end and an outlet end. Each layer of the material has a plurality of sperm selection microchannels. Each sperm selection microchannel has a respective microchannel inlet at the inlet end of the stack and extends to a respective microchannel outlet at the outlet end of the stack.

The stack can include at least 50 of the sperm selection microchannels, or between 50 and 100,000 of the sperm selection microchannels, or at least 6,500 of the sperm selection microchannels, or between 6,500 and 100,000 of the sperm selection microchannels.

The device can further include a core. The material can be wrapped around the core to form the stack. The core can be a cylindrical rod. The core can be conical and can taper in cross sectional area going from the inlet end towards the outlet end.

The device can further include a sperm collection reservoir at the outlet end. An outermost layer of the material can form the sperm collection reservoir.

The device can further include an inlet reservoir adjacent the inlet end.

The inlet end can be stepped.

The device can further include a second stack of a second plurality of layers of the material. The second stack can have a second inlet end and a second outlet end. The device can further include a sperm collection reservoir between the first stack and the second stack and adjacent the inlet end and the second inlet end.

At least some of the sperm selection microchannels can include a respective corner. At least some of the sperm selection channels can be triangular or trapezoidal in cross-section. A first set of the sperm selection channels can be triangular in cross-section, and a second set of the sperm selection channels can be trapezoidal in cross-section.

The material can be a polyethylene terephthalate film.

A kit of parts for selecting sperm is also disclosed. According to some aspects, a kit of parts for selecting sperm includes a device having a stack of a plurality of layers of a material. The stack has an inlet end and an outlet end. Each layer of the material includes a plurality of sperm selection microchannels. The sperm selection microchannels each have a respective microchannel inlet at the inlet end of the stack and extend to a respective microchannel outlet at the outlet end of the stack. The kit further includes a vessel having an interior volume. The device is connectable to the vessel to position the microchannel inlets in the interior volume. At least one of the device and the vessel provides a sperm collection reservoir in fluid communication with the microchannel outlets.

Methods for selecting sperm are also disclosed. According to some aspects, a method for selecting sperm includes: a. positioning a stack of a plurality of layers of a material in contact with a semen sample, so that a plurality of medium-filled sperm selection microchannels of the stack are in fluid communication with the semen sample; b. allowing sperm from the semen sample to swim longitudinally through the medium-filled sperm selection microchannels, from a microchannel inlet to a microchannel outlet of each respective sperm selection microchannel; and c. allowing the sperm to swim from the microchannel outlets into a medium-filled sperm collection reservoir adjacent the microchannel outlets.

Step a. can include positioning the stack in a vessel containing the semen sample. Step a. can include adding the semen sample to an inlet reservoir adjacent the medium-filled sperm selection microchannels.

The method can further include, prior to step a., filling the sperm selection microchannels with the medium.

The method can further include, prior to step c., filling the sperm collection reservoir with the medium.

Steps b. and c. can collectively include incubating the stack in contact with the semen sample for 5 to 90 minutes at about 37 degrees C.

Step b. can include allowing sperm from the semen sample to swim vertically through the medium-filled sperm selection microchannels.

Step b. can include allowing sperm from the semen sample to swim horizontally through the medium-filled sperm selection microchannels.

Step b. can include allowing the sperm from the semen sample to swim longitudinally through at least about 6,500 of the medium-filled sperm selection microchannels.

Methods for fabricating a sperm selection device are also disclosed. According to some aspects, a method for fabricating a sperm selection device includes a. creating a plurality of sperm selection microchannels in a material, wherein each sperm selection microchannel has a respective microchannel inlet and a respective microchannel outlet; and b. arranging the material into a stack of a plurality of layers of the material, so that the microchannel inlets are at an inlet end of the stack and the microchannel outlets are at an outlet end of the stack.

Step a. can include creating the sperm selection microchannels using laser ablation, cutting plotter engraving, cutting plotter scratching, soft lithography, injection molding, micromilling, micromachining, 3D-printing, xurography, wet etching, dry etching, powder blasting, sand blasting, polymer casting, sawing, stamping, and/or hot embossing.

Step b. can include wrapping the material around a core.

Step b. can include stacking discrete pieces of the material.

Step a. can include creating at least about 6,500 of the sperm selection microchannels.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 6 is a perspective view showing a first step of an example method for selecting sperm.

FIG. 7 is a perspective view showing a second step of the method of FIG. 6.

FIG. 8 is a perspective view showing a third step of the method of FIG. 6.

FIG. 11A is a cross section taken along lines 11A-11A in FIG. 10,

FIG. 11B is an enlarged perspective view of a portion of FIG. 11A, showing one of the sperm selection microchannels with sperm swimming therein.

FIG. 11C is an enlarged perspective view of a portion of FIG. 11A, showing one of the sperm selection microchannels with sperm swimming therein.

FIG. 11D is a fluorescent image of sperm swimming at the sharp corner of a triangular sperm selection microchannel.

FIG. 11E is an enlarged perspective view of a portion of FIG. 11A.

FIG. 12 is a perspective view showing a sixth step of the method of FIG. 6.

FIG. 13A is a perspective view of another example sperm selection device.

FIG. 13B is an enlarged view of a portion of the sperm selection device of FIG. 13A.

DETAILED DESCRIPTION

Figures 1A, 1B:
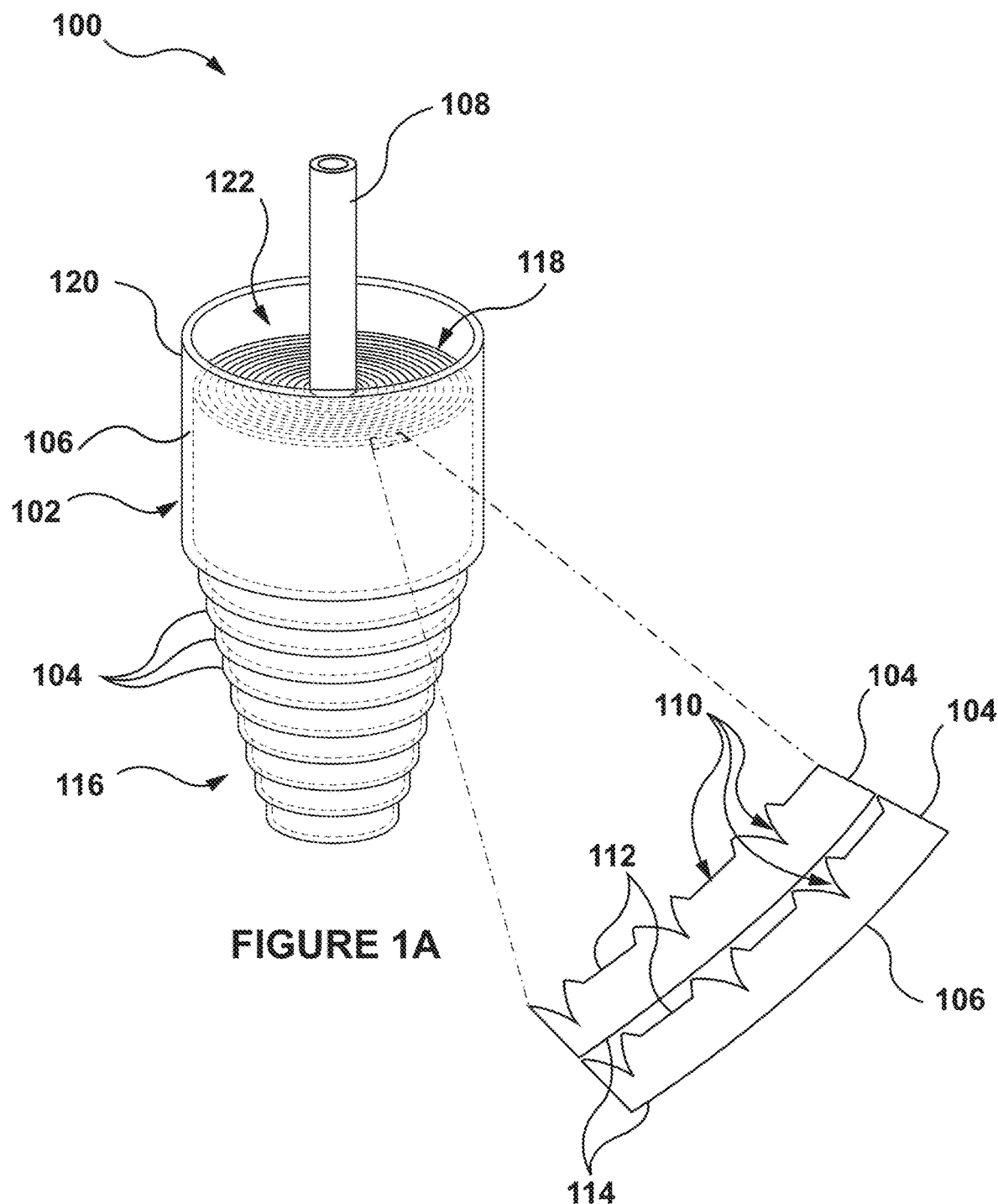
FIG. 1A is a perspective view of an example sperm selection device.
FIG. 1B is an enlarged view of a portion of the sperm selection device of FIG. 1A.

Various apparatuses or processes or compositions will be described below to provide an example of an embodiment of the claimed subject matter. No embodiment described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

As used herein, the term "sperm" is used as a short form for both "spermatozoon" and "spermatozoa". The term "sperm" can refer to human sperm or animal sperm (e.g. sperm from livestock).

As used herein, the term "semen sample" can refer to a raw semen sample, or a processed semen sample (e.g. a semen sample that has been diluted, or that has been frozen and thawed).

Generally disclosed herein are devices (and related kits and methods) that can be used in sperm selection—i.e. to select high- or top-quality sperm from a semen sample, based on the motility of the sperm in the semen sample. The devices disclosed herein can generally allow for motile or highly motile sperm to be separated from a semen sample containing seminal fluid, debris, dead sperm cells, and low- or no-motility sperm. The devices can be used, for example, in assisted reproduction (e.g. in in-vitro fertilization, intrauterine insemination or intracytoplasmic sperm injection), or in animal breeding.

In general, the devices disclosed herein can be relatively efficient, user-friendly, and practical for adoption into clinical practice. Furthermore, the devices disclosed herein can allow for a high throughput selection of sperm. Furthermore, the devices disclosed herein can separate sperm with high DNA integrity. For example, the DNA integrity of the selected sperm subpopulation can be improved up to 37.5% compared to existing techniques (as described in more detail below). For a raw sample of lower quality, yet higher improvement can be achieved. Furthermore, the devices disclosed herein can achieve both high selectivity (quality of sperm) and high yield (number of sperm). It is believed that the use of the devices disclosed herein may improve outcomes for male-infertility patients with poor semen quality.

In general, the devices disclosed herein can be in the form of 3-dimensional microfluidic devices—i.e. microfluidic devices in which microchannels are provided in more than one plane. Within a relatively small volume, the devices can provide, for example, 6,500 or more microchannels (referred to herein as "sperm selection microchannels") through which motile sperm can swim to create a separation of motile or highly-motile sperm from a semen sample. The sperm selection microchannels can mimic the internal structure of a human fallopian tube, as described in further detail below.

Referring now to FIG. 1A, a first example of a sperm selection device 100 (also referred to herein as a "device for selecting sperm", or simply as a "device") is shown. The sperm selection device 100 includes a stack 102 of several (i.e. a plurality of) layers 104 of a material 106 (only some of the layers 104 are labelled). In the example shown, the device 100 includes a core 108, and the material 106 is in the form of a single elongate piece of film that is wrapped around the core 108 multiple times to form the stack 102 of layers 104. In alternative examples (as will be described below with reference to FIGS. 13A and 13B) the material can be in the form of several discrete pieces of material that are laid on top of or next to each other to form the stack of layers. The stack 102 can include, for example, between about 2 and about 5000 layers 104 of the material 106 (e.g. about 15 layers, or about 30 layers, or about 240 layers, or about 1300 layers, or about 5000 layers). In the example shown, the material 106 is wrapped around the core 108 about 30 times, to create about 30 layers 104. The material 106 can be, for example, a plastic such as polyethylene terephthalate (PET), polyethylene, or polypropylene.

Referring to FIG. 1B, each layer 104 of the material 106 includes several (i.e. a plurality of) sperm selection microchannels 110 (only some of which are labelled). As used herein the term "sperm selection microchannel" refers to a channel that favors the passage of motile sperm as opposed to non-motile sperm. That is, motile and highly motile sperm can pass through a sperm selection microchannel 110 by swimming (e.g. in slither mode or bulk mode), but non-motile or low-motility sperm will not pass through a sperm selection microchannel in a significant amount.

In the example shown, each layer 104 of the material 106 includes a first surface 112 and a second surface 114. The sperm selection microchannels 110 are formed in the first surface 112 of each layer 104 (e.g. by using a cutting plotter, and/or by laser ablation, and/or by hot embossing), and the second surface 114 of each layer (except for the outermost layer) acts as a cover for the sperm selection microchannels 110 of an adjacent layer.

The sperm selection microchannels 110 can be of various shapes. In the example shown, the material 106 includes two sets of sperm selection channels: a first set that are generally triangular (also called "V-shaped") in cross-section, and a second set that are generally trapezoidal. In alternative examples, the material can include only triangular sperm selection microchannels, or only trapezoidal sperm selection microchannels, or sperm selection microchannels of another shape (e.g. rectangular or semi-circular).

The sperm selection microchannels 110 can be of various sizes. For example, the sperm selection channels can have a minimum width (i.e. a width at the narrowest point) of between about 2 microns and about 500 microns, a maximum width (i.e. a width at the widest point) of between about 5 microns and about 500 microns, and a height of between about 5 microns and about 500 microns. More specifically, in the example shown, for the trapezoidal sperm selection microchannels 110, the minimum width is about 160 microns, the maximum width is about 190 microns and the height is about 20 microns. Furthermore, in the example shown, for the triangular sperm selection microchannels 110, the minimum width is about 5 microns, the maximum width is about 60 microns, and the height is about 70 microns.

It is believed that the sperm selection microchannels 110 of the sizes and shapes described herein can mimic the interior of a fallopian tube by providing sharp corners. In turn, this is believed to select strong-swimming sperm. Particularly, it is believed that sharp corners can isolate and guide sperm for several centimeters. It is believed that because of the sharp corners (e.g. V-groove channels feature a triangular cross-section with an elongate, narrow section at the tip having a width of less than 10 microns, considering a typical sperm head is 4.4 microns in length and 2.8 µm in width), sperm is confined to a single dimension and swim in an almost straight line along the sperm selection microchannels 110 (as shown in FIGS. 11B, 11C and 11D, described in further detail below).

The sperm selection microchannels 110 can be relatively tightly packed, and the material 106 can be relatively thin (e.g. between about 3 microns thick and about 400 microns thick, or about 20 microns thick, or about 60 microns thick, or about 240 microns thick, or about 120 microns thick as in the example shown), so that the device 100 can be relatively small (e.g. having a diameter of less than about 20 mm, e.g. about 13 mm in the example shown), while still including a relatively large amount of sperm selection microchannels 110. For example, the device can include between 50 and 100,000 sperm selection microchannels, or between 6,500 and 100,000 sperm selection microchannels. In the example shown, the device 100 has about 6,500 of the sperm selection microchannels 100.

Referring still to FIG. 1A, the stack 102 can have an overall length of, for example, between about 5 mm and about 40 mm (i.e. about 29 mm in the example shown, where the stepped inlet end 116 (described below) has a length of 19 mm, and the remainder of the stack has a length of 10 mm). The dimensions may be selected to allow the device 100 to fit within a standard 14 mL test tube.

Referring still to FIG. 1A, the stack 102 has an inlet end 116 and an outlet end 118. Each sperm selection microchannel 110 has a microchannel inlet (not shown) at the inlet end 116 of the stack 102, and extends to a microchannel outlet (not shown) at the outlet end 118 of the stack 102. In the example shown, the microchannel inlets and the microchannel outlets are defined by open ends and/or end portions of the sperm selection microchannels 110.

In the example shown, the sperm selection microchannels 110 are generally linear, and each sperm selection microchannel 110 has only one respective microchannel inlet and only one respective microchannel outlet. In alternative examples, the sperm selection microchannels can be of another configuration, such as branched. For example, a sperm selection microchannel can branch between the inlet end and the outlet end of the stack so that the sperm selection microchannel has a plurality of branches at the inlet end, which combine into one main branch at the outlet end. In such examples, the sperm selection microchannels can each have, respectively, a plurality of microchannel inlets and/or a plurality of microchannel outlets.

Figure 2:
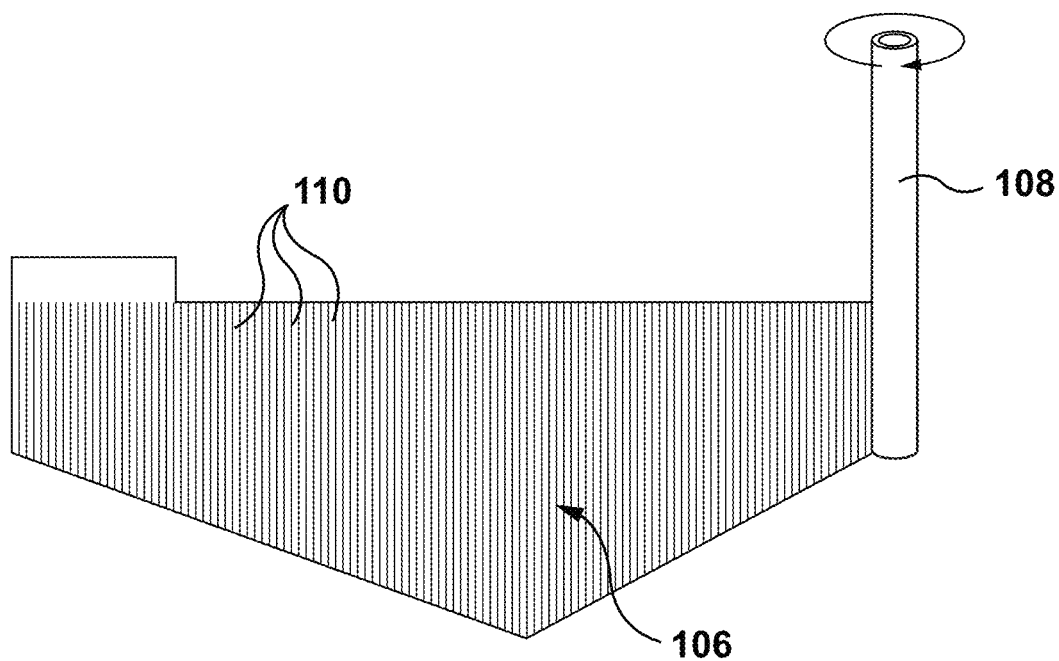
FIG. 2 is a plan view showing the shape of a material that when wrapped around a cylindrical core, yields the sperm selection device of FIG. 1A.

As mentioned above, in the example shown, the material 106 is in the form of a single elongate piece of film that is wrapped around a core 108 multiple times to form the stack 102 of layers 104. In the example shown, the material 106 is shaped so that when wrapped, the inlet end 116 of the stack 102 is stepped. This can provide an increased contact area between a semen sample and the inlet end 116, and particularly between the microchannel inlets and the semen sample (as shown in FIG. 11E), which can maximize or increase the number of sperm that can enter the sperm selection microchannels 110. The material 106 is further shaped so that when wrapped, the outermost layer 120 of the stack 102 forms a sperm collection reservoir 122 at the outlet end 118. An example shape of a material 106 that, when wrapped, can provide the stepped inlet end 116 and the collection reservoir 122, is shown in FIG. 2.

Figure 3:
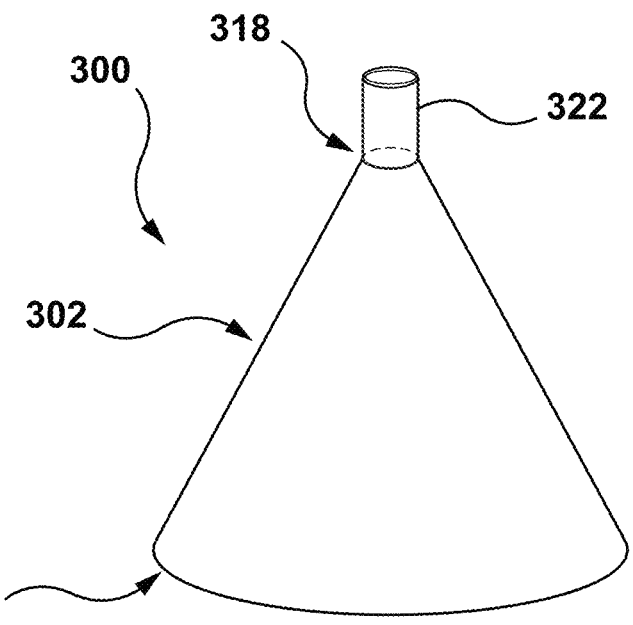
FIG. 3 is a perspective view of another example sperm selection device.

Referring back to FIG. 1A, in the example shown, the core 108 is generally cylindrical. For example, the core 108 can be a cylindrical glass tube. The core 108 has a central bore, which can allow for escape of air in use, as described below. An alternative example is shown in FIG. 3, in which the core (not visible) of the sperm selection device 300 is generally conical, to yield a conical stack 302. The stack 302 tapers in cross-sectional area from the inlet end 316 of the stack 302 towards the outlet end 318 of the stack. This conical shape can facilitate the selection of sperm from a relatively large volume into a relatively small sperm collection reservoir 322. This can allow for the concentration of a relatively large amount of motile sperm.

Figure 4:
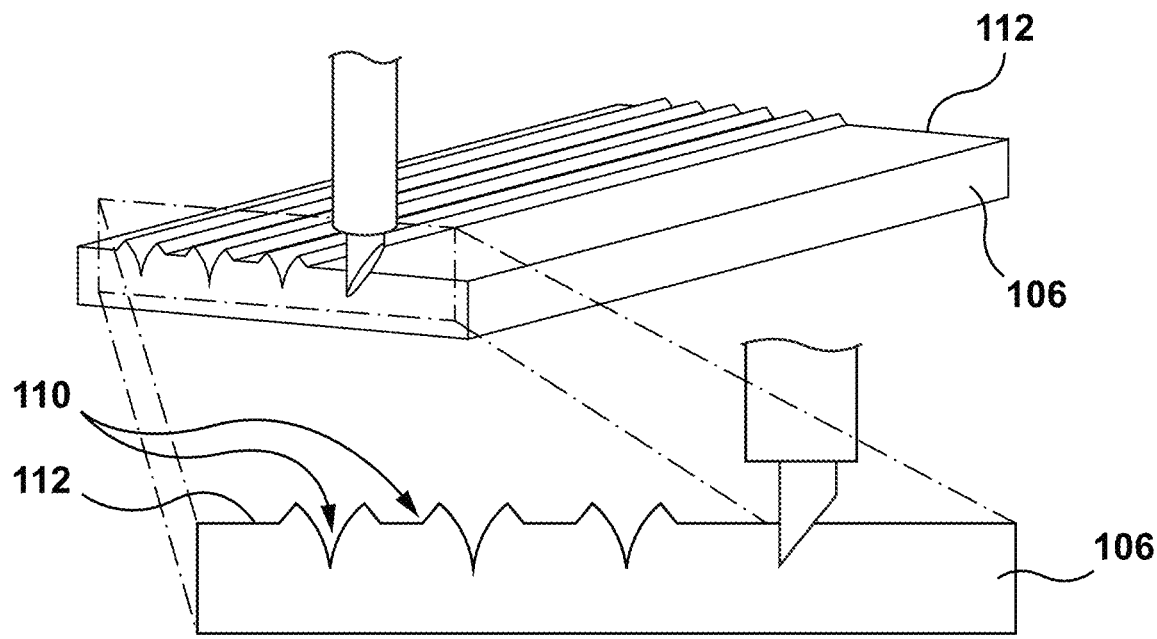
FIG. 4 is a perspective view showing a step of an example method for fabricating a sperm selection device.
Figure 5:
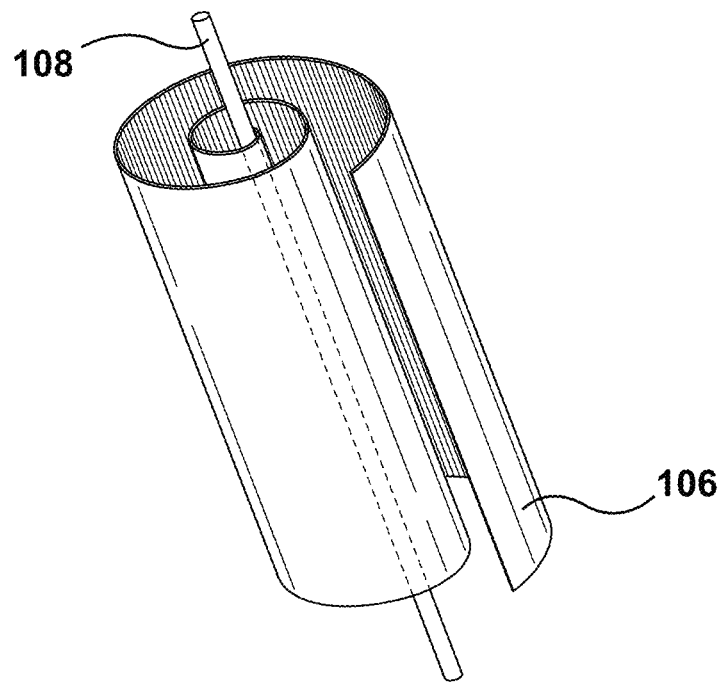
FIG. 5 is a perspective view showing a subsequent step of the method of FIG. 4.

Referring now to FIGS. 4 and 5, an example method for fabricating the sperm selection device 100 of FIG. 1A will be described. In general, the sperm selection device 100 can be fabricated by creating a plurality of sperm selection microchannels 110 in a material 106, and then arranging the material 106 into a stack of layers. The sperm selection channels 110 can be created in the material 106, for example, using a cutting plotter (i.e. to scratch or engrave the first surface 112 of the material 106, as shown in FIG. 4), laser ablation (i.e. to pattern the first surface of the material), hot embossing (i.e. to pattern the first surface of the material), soft lithography, injection molding, micromilling, micromachining, 3D-printing, xurography, wet etching, dry etching, powder blasting, sand blasting, polymer casting, sawing, and/or stamping. To arrange the material 106 into a stack of layers, the material 106 can then be wrapped around a core 108 (as shown in FIG. 5). In the example shown in FIG. 5, the core 108 is cylindrical; however as previously mentioned, in alternative examples the core can be another shape such as conical. The material 106 can be held in the wrapped shape for example with the use of adhesives, or tape, or by heat treatment.

Referring now to FIGS. 6 to 13, a method for selecting sperm will be described. The method will be described with reference to the device 100 of FIG. 1A; however, the method is not limited to the device 100, and the device 100 is not limited to use according to the described method.

In general, the method can include positioning the stack 102 of the device 100 in contact with a semen sample, so that the sperm selection microchannels 110 of the stack 102, which are medium-filled, are in fluid communication with the semen sample; allowing sperm from the semen sample to swim longitudinally through the medium-filled sperm selection microchannels 110, from the microchannel inlets to the microchannel outlets; and allowing the sperm to swim from the microchannel outlets into the sperm collection reservoir 122, which is also medium-filled.

More specifically, referring first to FIG. 6, the sperm selection microchannels 110 (not visible in FIG. 6) can first be filled with a sperm processing medium (also referred to herein simply as a "medium"). Various sperm processing media may be used, such as PureSperm® Wash (Nidacon, Canada), GYNOTEC SpermWash® medium (Fertitech, Canada), G-IVF™ (Vitrolife), Sperm Preparation Medium (Origio, Denmark), and/or Ham's F10 (Biochrome, Germany). In order to fill the sperm selection microchannels 110 with the medium, the sperm selection device 100 can, for example, be incubated in a container 600 (e.g. a test tube or vial) containing the medium, for example at about 37 degrees C. and for about 10 minutes. Alternatively, the sperm selection device 100 can be provided (e.g. sold) with the sperm selection microchannels 110 pre-filled with the medium.

Referring next to FIG. 7, the stack 102 of the device 100 can then be placed in contact with a semen sample 700, so that the medium-filled sperm selection microchannels 110 (not visible in FIG. 7) are in fluid communication with the semen sample 700. This can be done, for example, by inserting or otherwise positioning the stack 102 in the interior volume of a vessel 702 containing the semen sample 700, so that the inlet end 116 is in contact with the semen sample 700. The vessel 702 can be, for example, a test tube, a vial, or a petri dish. In some examples, the vessel 702 is a test tube in which the semen sample is already being stored (e.g. a commercially available 14 mL test tube used for semen collection and storage). In the example shown, the vessel 702 is a test tube, and the stack 102 is sized to fit snugly within the interior volume of the test tube, so that it is held up by the test tube. Furthermore, the stack 102 is sized so that in general (e.g. for use with a semen sample having volume of about 1 mL), the inlet end 116 of the stack 102 is in contact with the semen sample 700, while the outlet end 118 of the stack 102 is spaced away from the semen sample 700. It is believed that as the sperm selection microchannels 110 are filled with medium when the stack 102 is inserted in the semen sample 700, the microchannel outlets (not visible in FIG. 7) act as a capillary stop valve, which prevents fluid flow in the sperm selection microchannels 110 (not visible in FIG. 7) during insertion into the semen sample 700. During insertion of the stack 102 into the semen sample 700, air can escape via the central bore in the core 108.

Referring next to FIG. 8, the sperm collection reservoir 122 of the device 100 can then be filled with medium, for example using a pipette to add approximately 1 mL of medium to the sperm collection reservoir 122. Alternatively, the sperm selection device 100 can be provided (e.g. sold) with the sperm collection reservoir 122 pre-filled with the medium. Medium from the sperm collection reservoir 122 can also fill any gaps between the stack 102 and the semen sample 700.

Figure 9:
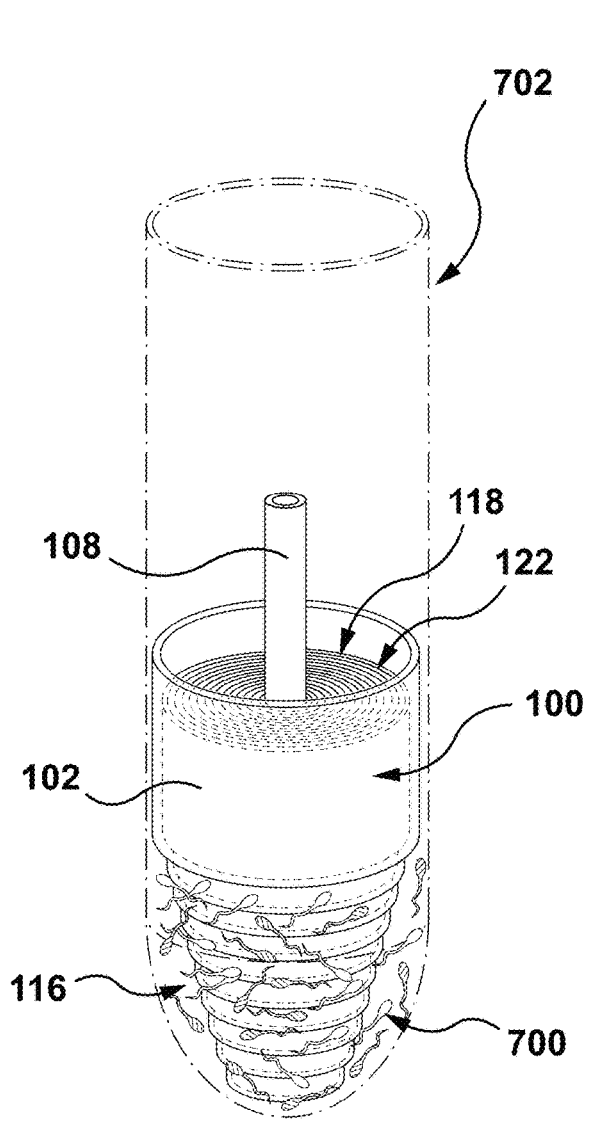
FIG. 9 is a perspective view showing a fourth step of the method of FIG. 6.
Figure 10:
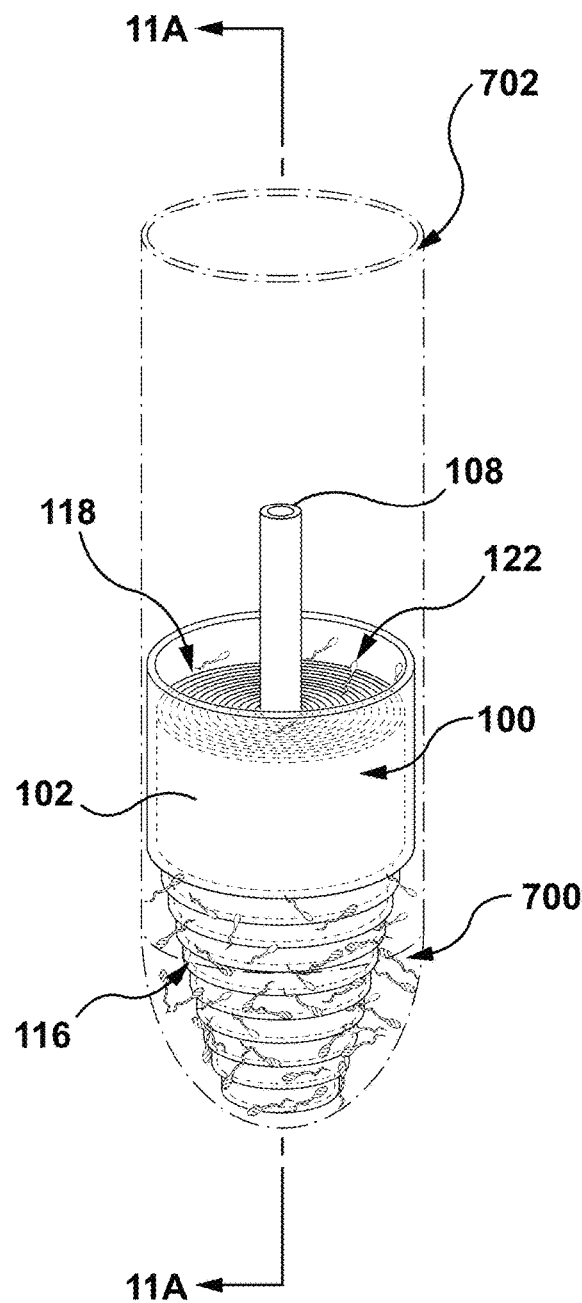
FIG. 10 is a perspective view showing a fifth step of the method of FIG. 6.

Referring next to FIGS. 9 and 10, sperm can then be allowed to swim from the semen sample 700, longitudinally through the medium-filled sperm selection microchannels 110 (i.e. from the microchannel inlet to a microchannel outlet of each respective sperm selection microchannel 110), and from the microchannel outlets into the medium-filled sperm collection reservoir 122. This can be achieved, for example, by incubating the stack 102 in contact with the semen sample for 5 to 90 minutes, at body temperature (i.e. between about 35 degrees C. and 40 degrees C., and preferably at about 37 degrees C.).

Referring to FIGS. 11A to 11E, during incubation, motile or high-motility sperm can swim through the sperm selection microchannels 110 to the sperm collection reservoir 122, while non-motile or low-motility sperm will generally remain in the semen sample 700, thereby separating the motile or high-motility sperm from non-motile or low-motility sperm. Due to the high number of sperm selection microchannels 110, a high number of motile or high-motility sperm can swim to the sperm collection reservoir 122 in a relatively short time frame. Furthermore, as shown in FIGS. 11B and C, due to the relatively sharp corners provided by the sperm selection microchannels 110, motile sperm are guided to swim an almost straight line along the sperm selection microchannels 110. A fluorescent image of sperm swimming at the sharp corner of a triangular microchannel is shown in FIG. 11D. Furthermore, as shown in FIG. 11E, the stepped inlet end 116 of the stack allows for the sperm to readily access the sperm selection microchannels 110, which can allow for a higher quantity of high-motility sperm to reach the sperm collection reservoir 122.

In the example shown, the sperm swim vertically through the medium-filled sperm selection channels 110. In alternative examples, the sperm can swim horizontally or diagonally through medium filled sperm selection channels.

Referring next to FIG. 12, the selected sperm (i.e. the sperm that have reached the sperm collection reservoir 122) can then be removed from the sperm collection reservoir 122 (e.g. using a pipette) for use, e.g. in assisted reproduction.

Referring now to FIGS. 13A and 13B, another example of a sperm selection device is shown. Features in FIGS. 13A and 13B that are like those of FIG. 1 will be referred to with like reference numerals, incremented by 1200.

Similarly to the sperm selection device of FIG. 1A, the sperm selection device 1300 of FIGS. 13A and 13B includes a stack 1302a of several layers 1304a of a material, where the stack has an inlet end 1316a and an outlet end 1318a, and where each layer 1304a of the material includes several sperm selection microchannels 1310a (shown in FIG. 13B). However, the device of FIG. 13 further includes a second stack 1302b of several layers 1304b of the material, where the second stack 1302b has an inlet end 1316b and an outlet end 1318b, and where each layer includes several sperm selection microchannels (not shown). The first stack 1302a and second stack 1302b are positioned so that the microchannel outlets (not shown) of each stack 1302a, 1302b face towards each other. That is, in the example shown, the sperm selection microchannels of each stack extend horizontally (i.e. so that in use, sperm swim horizontally through the sperm selection microchannels). A space between the first stack 1302a and the second stack 1302b forms a sperm collection reservoir 1322 between the first stack 1302a and the second stack 1320b. The device 1300 further includes a pair of inlet reservoirs 1324a, 1324b, one of which is adjacent the inlet end 1316a of the first stack 1302a, and one of which is adjacent the inlet end 1316b of the second stack 1302b.

The sperm selection device of FIGS. 13A and 13B may be used in a similar fashion to that of FIGS. 1A and 1B; however, rather than inserting the device into a vessel containing a semen sample, a semen sample can be deposited into the inlet reservoirs 1324a, 1324b (e.g. using a pipette). The sperm can then be allowed to swim horizontally through the sperm selection microchannels towards the sperm collection reservoir 1322.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

Examples

Materials & Methods
Sperm Selection Device Fabrication

Sperm selection devices as shown in FIGS. 1A and 1B were fabricated as follows:

Cutting patterns for the sperm selection microchannels were drawn using AutoCAD software. A cutting plotter (Silhouette America Inc., UT, USA) was used to scratch the designs on the surface of 100-micron thick polyethylene terephthalate (PET) films (McMaster-Carr, OH, USA) to make the V-shaped sperm selection microchannels. The patterned film was cut to shape (as shown in FIG. 2). The film was rolled up around a glass tubing with a 5 mm outer diameter and a 3 mm inner diameter (Ginsberg Scientific) to fabricate the sperm selection device. A piece of adhesive PCR sealing tape (Sarstedt, Nümbrecht, Germany) was used to hold the device together after rolling.

Semen Sample Preparation

Cryogenically frozen human donor samples were purchased from ReproMed Ltd and stored in a −80 degrees C. freezer. The samples were thawed 30 minutes prior to each experiment in a 37 degrees C. water bath. Donor samples were diluted with PureSperm® Wash (Nidacon, Canada) at a 1:6 ratio to simulate a male infertility patient sample characteristic and obtain enough sample volume for running side-by-side sperm selection experiments.

For patient samples, fresh ejaculated human semen was obtained by masturbation after 2-4 days of sexual abstinence from Hannam Fertility Centre (Toronto, Canada). The samples were incubated at 37 degrees C. for 30 min to allow liquefaction. All patients provided an informed consent for research studies according to the regulation of the Assisted Human Reproduction Act.

Sperm Selection

First, the sperm selection device was inserted in a 20-mL vial (VWR, Canada) containing 10 mL of PureSperm® Wash (Nidacon, Canada) to fill the sperm selection microchannels. 1 mL of semen sample was placed in a 14 mL round bottom test tube (Falcon, Corning, NY, USA). The device, with medium-filled sperm selection microchannels, was then inserted into the test tube on top of the semen sample. Then, 1 mL of PureSperm® Wash pipetted into the sperm collection reservoir. After 1 hr incubation at 37 degrees C., selected sperm suspension was collected from the sperm collection reservoir for concentration and DNA integrity assessment.

Sperm Selection Via Density Gradient Concentration (DGC) and Swim Up (SU)

Sperm selection via density gradient concentration (DGC) and swim up (SU) was used as a control.

First, density gradient centrifugation was performed using a 1:1:1 ratio of the semen sample, PureSperm®40, and PureSperm®80 (Nidacon, Canada) at 500 g for 15 minutes. Then, the pellet was resuspended in PureSperm® Wash (Nidacon, Canada) and centrifuged at 300 g for 5 minutes. The washing step was repeated one more time. The final pellet was resuspended in ~50 microlitres of PureSperm® Wash and layered below 1 mL of PureSperm® Wash in a 5-mL round bottom test tube (Falcon, Corning, NY, USA). It was incubated for 60 minutes at 37° C. Finally, 200 microlitres of cell suspension was collected from the top layer of the solution for DNA integrity testing.

Sperm DNA Integrity Assessment

SpermFunc® DNAf kit (Fertitech, QC, Canada) was used to assess the DNA integrity of sperm cells by following the manufacturer's instructions. 60 microlitres of sperm sample was dissolved into 140 microlitres of low melting point agarose gel. Then, 30 microlitres of cell suspension in the gel was dispensed onto the pre-coated slides and covered with a glass coverslip. The gel was solidified at 2-8 degrees C. for 5 min. After removing the glass cover, the slide was incubated in solution A for 7 min at room temperature. Then, it was incubated in solution B for 25 min. After rinsing the slide with water, it was washed with 70%, 90%, and 100% ethanol solutions. Finally, it was incubated for 15 min in a solution mixture of Wright's stain and Wright's buffer. After staining, it was washed with water and air-dried. An EVOS FL Auto microscope (Life Technologies, CA, USA) and AxioScan.Z1 slide scanner (Zeiss, Germany) with 40× magnification were used to capture brightfield images. Image analysis was performed by a developed Python code (described below) to measure the size of the halo and sperm head.

Concentration Measurement

Concentration and motility of the donor and patient samples were measured and reported by ReproMed Ltd. (Etobicoke, ON, Canada) and the Hannam Fertility Centre (Toronto, ON, Canada), respectively. To measure the concentration of the selected sperm samples, sperm samples were heated for ~5 min to immobilize all the cells. Then, 1 microlitre of propidium iodide (PI) (Invitrogen, NY, USA) was added to 100 microlitres of sperm sample and incubated for 8 min at 37 degrees C. 10 microlitres of the sample was loaded into each counting chamber of a Neubauer improved hemocytometer. The EVOS FL Auto microscope (Life Technologies, CA, USA) with 10× magnification and an RFP (ex.: 531/40 nm, em.: 593/40 nm) filter was used to count the cells.

Imaging Sperm Movement in Sperm Selection Microchannels

A piece of 100-micron thick polyethylene terephthalate (PET) film was scratched with the cutting plotter (as described above) and covered with another piece of PET film. Then, the films were sandwiched between a glass slipcover (VWR, Canada) and a PMMA sheet (1 mm thick) using double-sided tape (Microfluidic diagnostic tape 9965, 3M™, MO, USA). A thawed donor sperm sample was labeled with the LIVE/DEAD sperm viability kit (L-7011, Invitrogen, NY, USA). According to the suggested protocol by the manufacturer, 1 microlitre of diluted SYBR 14 (1:50 in PureSperm® Wash) was added to the sperm sample to stain live sperm cells. After 5 min incubation at 37 degrees C., 1 microlitre of propidium iodide (PI) was added (dead cells stain) and allowed to incubate for 5 min at 37 degrees C. Labeled cells were loaded into the fabricated device described above. Sperm cell locomotion inside the microchannels was imaged using an EVOS FL Auto microscope (Life Technologies, CA, USA) with 20× magnification and GFP (ex.: 470/22 nm, em.: 525/50 nm) and RFP (ex.: 531/40 nm, em.: 593/40 nm) filters.

Design of Experiments

For performing all sperm selection experiments using the donor and infertility patient semen samples, the raw sample was split for side-by-side testing of the sperm selection device with the DGC+SU method. In experiments with donor samples, 1 mL of the diluted sample was used for the sperm selection device, and 1 mL of the sample was processed by DGC+SU. In clinical testing, the sperm selection device was performed using 1 mL of fresh patient semen samples. Depending on the initial volume of the patient sample, the leftover volume (up to 1 mL) was used for DGC+SU.

Statistical Analysis

Differences between average B/A were tested using the two-tailed t-test, and p-values were calculated using the SciPy library of Python. For % DFI results, two-sided Fisher's exact test was used to find p-values. Fisher's exact test and Clopper-Pearson confidence interval of all % DFI results were done using R software. In all statistical analyses, it was assumed that treatment results were independent. $p<0.05$ was considered as the cutoff for significance.

Results

Design, Fabrication, and Operation of Sperm Selection Device

Figure 14:
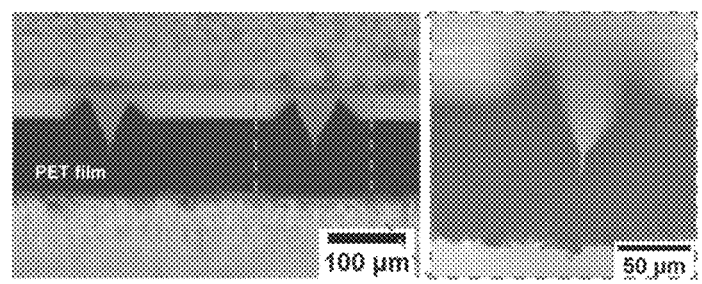
FIG. 14 shows cross-section microscope images of V-shaped sperm selection microchannels.
Figure 15:
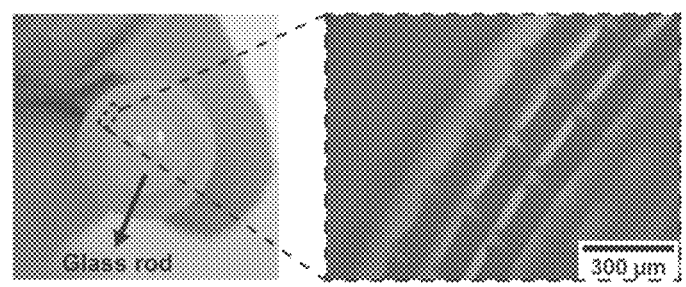
FIG. 15 shows rolled-up scratched polyethylene terephthalate (PET) film, which is filled with sperm washing medium containing fluorescein dye.

To fabricate the sperm selection device, the surface of a piece of PET film was scratched using a cutting plotter (i.e. as shown in FIG. 4). This scratching formed V-shaped sperm selection microchannels with a minimum width of less than 10 microns. Cross-sectional microscope images of sperm selection microchannels are shown in FIG. 14. The scratched film was wrapped around a glass rod core to form the sperm selection device (as shown in FIG. 15), with a very high density of triangular and trapezoidal microchannels. The device had greater than 6,500 sperm selection microchannels, with about 23,000 sharp corners.

With the hydrophilic nature of the PET film, capillary pressure was sufficient to fill all the sperm selection microchannels with fluid by simply introducing the device into the sperm processing media. FIG. 15 shows the channels filled with sperm processing medium (PureSperm® Wash) containing fluorescein dye. One end of the sperm selection microchannels was in contact with the medium, and the image was taken from the other end.

Performance for Sperm Selection

To minimize or ensure the absence of fluid flow inside the device, the selection method was tested several times with dead sperm samples. In all experiments, no dead cells could be found in the collection reservoir after up to 2 hours of incubation. This shows that non-motile sperm cannot or do not readily or tend not to pass through the sperm selection microchannels and reach the sperm collection reservoir in any significant amount.

Sperm DNA fragmentation is an indicator for male infertility as it can show sperm genetic defects which are associated with failures in embryo development, implantation, and pregnancy rate. In this study, the DNA integrity of sperm samples was assessed via the sperm chromatin dispersion (SCD) assay as a measure of sperm quality and fertilization capacity. In the SCD test, sperm nucleoids are dispersed into the agarose gel. Sperm with less DNA breakage produce a larger halo of spreading DNA, and the size of the DNA halo is a measure of sperm DNA fragmentation. The SCD assay was chosen as it is well-suited to evaluating samples with a low number of sperm, and offers a good correlation with other clinical sperm DNA fragmentation tests like Sperm Chromatin Dispersion Assay (SCSA) and TdT-mediated-dUTP nick end labeling (TUNEL). Flow cytometry-based assays require several thousand cells for each test.

Figure 16:
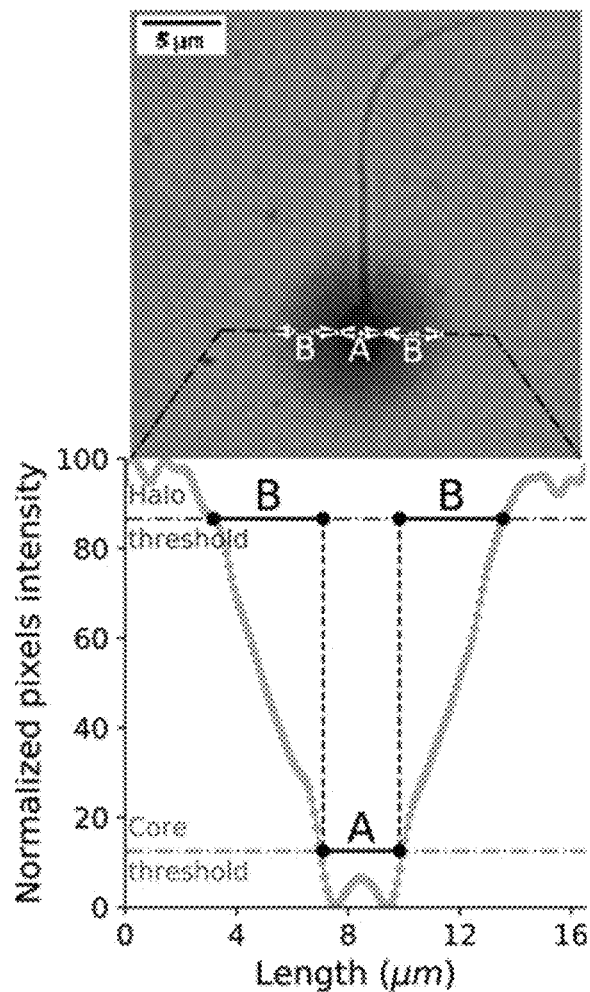
FIG. 16 shows the developed python code method for Sperm Chromatin Dispersion (SCD) assay analysis. The software looked at the normalized intensity of pixels at a perpendicular line to the sperm head direction. Based on two thresholds (halo and core threshold), sperm minor diameter and the DNA halo width are found.

In addition, computer software was developed that can find sperm in the SCD images using an adaptive thresholding algorithm and measure the minor diameter of the sperm head (A) and the DNA halo width (B), as shown in FIG. 16. The thresholds were obtained by comparing the software results with known values from manual measurements using the ImageJ software. Normalized halo width to the minor diameter of sperm head (B/A) is used to score sperm DNA quality at the single-cell level; the higher the B/A, the higher the sperm DNA quality. The DNA fragmentation index (DFI) indicates the percentage of sperm with B/A<=1/3, as a measure of sperm population quality.

Figure 17:
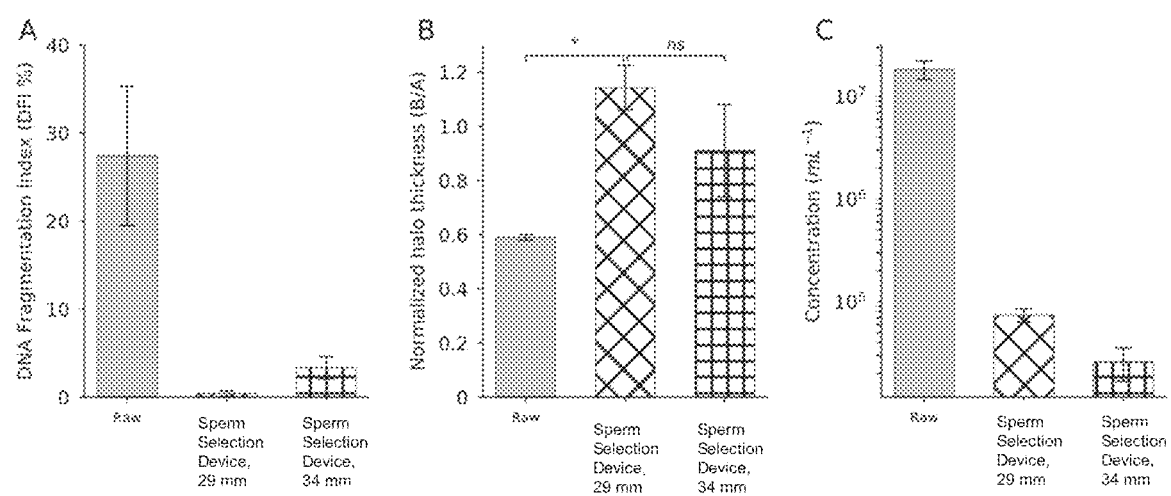
FIG. 17 shows sperm selection performance of sperm selection devices with 10 mm and 15 mm microchannel lengths. Panel A shows the percentage of DNA fragmentation index (DFI), panel B shows the Normalized DNA halo thickness, and panel C shows the concentration of raw and selected sperm samples. Error bars represent the sampling error of measurements (N=3 different donor samples). $*p<0.05$ compared to the DGC+SU. ns $p>0.05$.

Two devices, one with a 29-mm length (where 19-mm accounts for the length of the stepped inlet end of the stack, and 10-mm accounts for the length of the remainder of the stack, as shown in FIG. 1A) and one with a 34-mm length (where 19-mm accounts for the length of the stepped inlet end of the stack, and 15-mm accounts for the length of the remainder of the stack), were tested with donor human sperm samples. By increasing the length of the stack, no significant improvement in the sperm DNA quality could be observed (FIG. 17, panels A and B). With the 29 mm length, more sperm cells could be retrieved after the selection process (FIG. 17, panel C). Therefore, a 29-mm length was chosen for the rest of the experiments.

Figure 18:
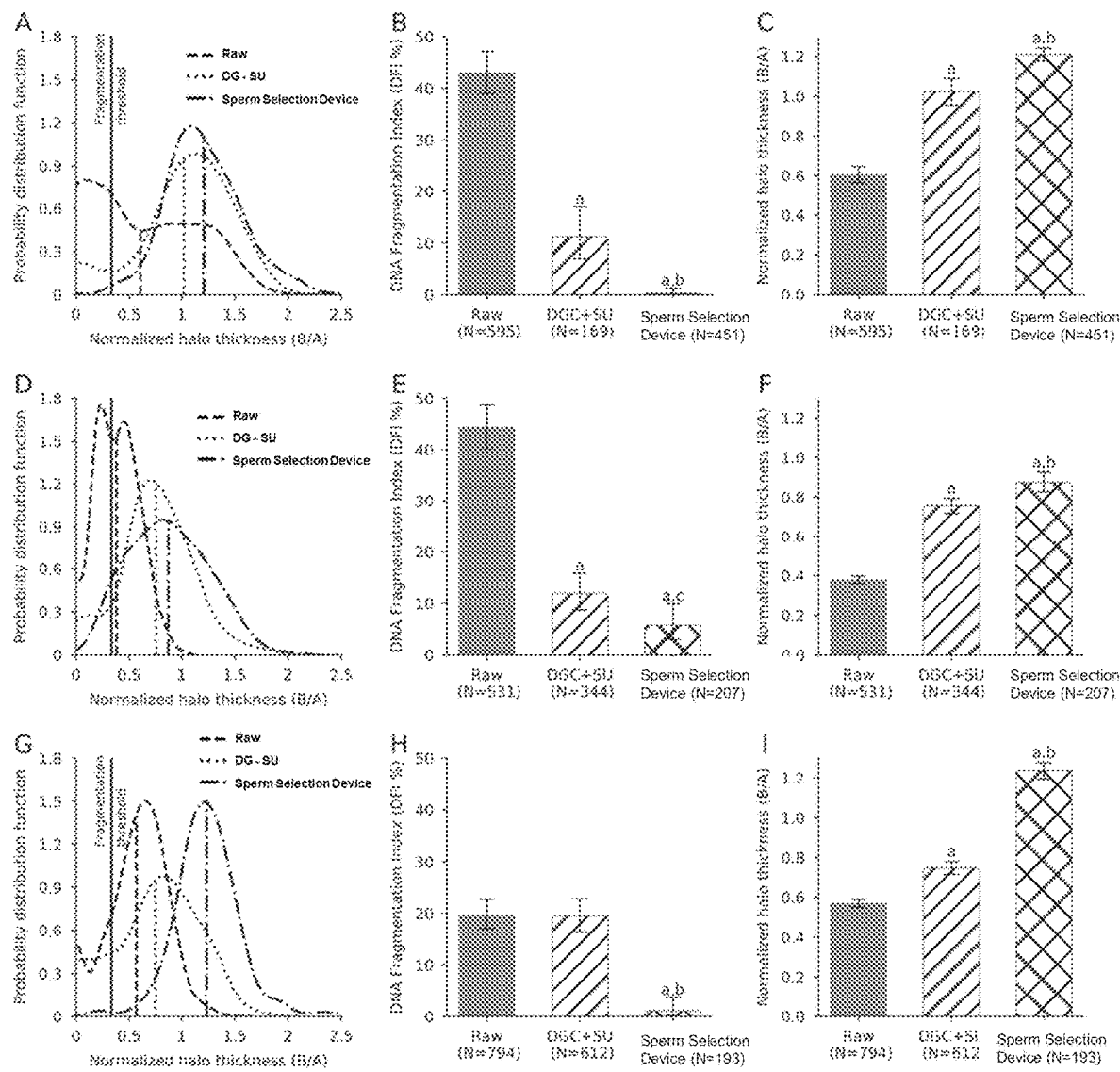
FIG. 18 shows SCD assay results for the donor samples experiments. Panels A, D, and G show the estimated probability distribution function of normalized DNA halo thickness of sperm (Box and swarm plot of all results are provided in FIG. 19). The fragmentation threshold defined by the SCD standard protocol (B/A<=1/3) is demonstrated as a solid line. The vertical dashed lines represent the average B/A value of the correspondent sample. Panels B, E, and H show DNA fragmentation index and panels C, F and I show average normalized DNA halo thickness of raw and selected sperm. Error bars represent 95% confidence interval. a $p<0.001$ compared to raw; b $p<0.001$ compared to DGC+SU; c $p<0.02$ compared to DGC+SU.
Figure 19:
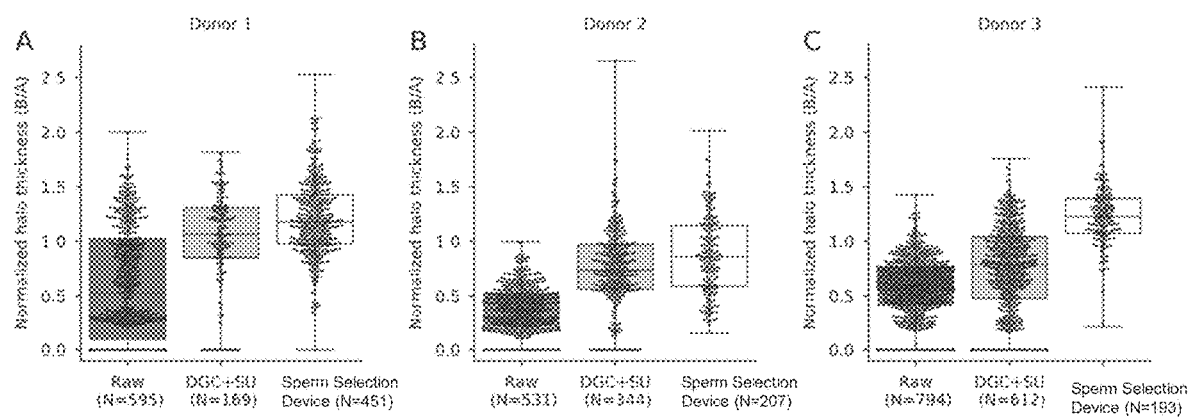
FIG. 19 shows SCD assay results for the donor samples experiments. The box plot demonstrates the first quartile, median, and third quartile values as three horizontal lines of the box. The whiskers show the lowest and the largest data points.

To investigate the performance of the sperm selection device, it was tested with thawed donor sperm samples. Donor samples contain sperm cells with very low to high quality, so testing with these samples can show how a device performs with sperm having different qualities. All donor samples were diluted to have 3 to 5 million/mL motile sperm concentration to simulate a male infertility patient sample with low motile sperm concentration and to obtain enough sample volume to split the diluted sample for selection with the sperm selection device and DGC+SU. The device performance was benchmarked with the standard clinical practice, DGC+SU. FIG. 18 shows the SCD test results of experiments performed with three different donor samples. Probability distribution function (PDF) of B/A for raw semen as well as selected sperm using the sperm selection device and DGC+SU is shown in the first column of FIG. 18. After both selection processes, dead cells are left behind and sperm with higher quality is isolated, so a reduced PDF for small B/A and an increase PDF for larger B/A in selected samples is seen (outcomes of DGC+SU and sperm selection device). Comparing the B/A PDF of the selected sperm using the sperm selection device to that of raw and DGC+SU samples, it has the least distribution for B/A<=1/3 (FIG. 18, panels A, D, and G), which results in a significant improvement in % DFI (FIG. 18, panels B, E, and H). Compared to the % DFI of DGC+SU outcome, there was a 98%, 51%, and 94% improvement by using the sperm selection device for all three donor samples, respectively. It has been shown that sperm cells with B/A>1 have very low DNA breaks and high DNA quality. In FIG. 18, panels A, D, and G, it can be seen that the distribution of sperm with large halo (B/A>1) is amplified in the sperm selection device outcome compared to the raw and DGC+SU. Having fewer fragmented cells (B/A<=1/3) and more high-quality sperm (B/A>1) results in a significantly higher average B/A for the selected sperm using the sperm selection device (FIG. 18, panels C, F, and I). All these measures indicate significantly higher DNA integrity for the sperm selection device outcome. Box and swarm plot of all results are provided in FIG. 19.

In using the sperm selection device, sperm did not experience significant external forces (e.g. centrifuge). However, in the conventional clinical practice (DGC+SU), there are 3 steps of centrifugation (1 step DGC following by 2 steps of washing). Also, centrifugation steps can generate reactive oxygen species which can damage sperm DNA quality. The absence of centrifugation in the sperm selection method described herein is believed to be one reason for the observed significant improvement in the selected sperm DNA quality compared to the DGC+SU. Also, micro confinements and sharp corners in the sperm selection device can mimic the sperm selection path in the female reproductive tract, and it is believed that only highly-motile, strong sperm can traverse through the selection paths and swim the length of the device up to the sperm collection reservoir. It is believed that the length of the sperm selection microchannels was not too long to exhaust and damage the cells, nor too short that even low-quality sperm could pass through. The sperm selection device provided an approach that isolated sperm with very high DNA quality and filtered out debris, dead cells and most of the low-quality sperm.

Clinical Testing Results

Figure 20:
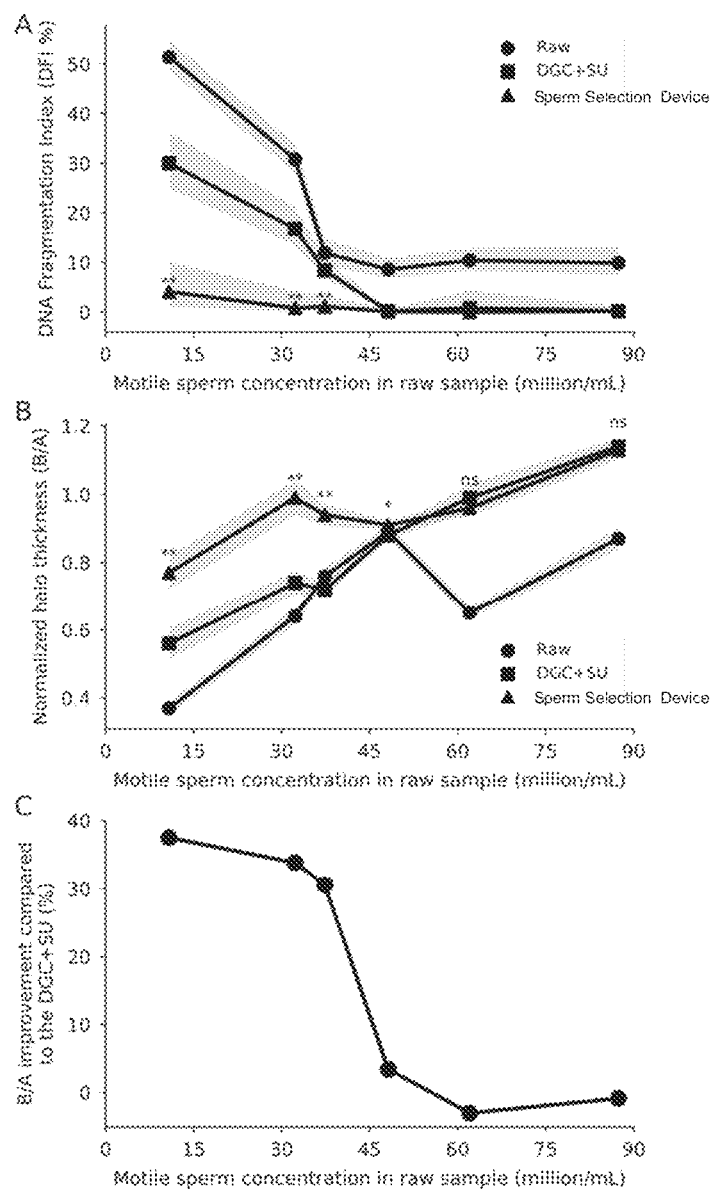
FIG. 20 shows SCD assay results of side-by-side clinical testing of a sperm selection device with DGC+SU. Panel A shows the DNA fragmentation index and panel B shows the average normalized DNA halo thickness of raw patient samples and selected sperm using the sperm selection device and DGC+SU. The shadows represent 95% confidence interval. ** $p<0.001$ compared to the DGC+SU. *$p<0.005$ compared to the DGC+SU. ns $p>0.05$. Panel C shows percentage improvement in the average normalized DNA halo thickness of selected sperm achieved by using the sperm selection device compared to the DGC+SU. (The estimated probability distribution function of data and box and swarm plots of all results are provided in FIGS. 21 and 22)

At the next step, the sperm selection device was tested side-by-side with the current best clinical practice (DGC+SU) using fresh infertility patient semen samples at the Hannam Fertility Centre in Toronto, ON. Samples with different qualities were tested to establish the device performance at different conditions. FIG. 20, panel A, shows the % DFI of the raw patient samples and selected sperm using the sperm selection device and DGC+SU method vs the motile sperm concentration of raw semen. There is a negative correlation between the % DFI and motility of raw samples, as is common. By performing the DGC+SU process, dead sperm and some of the low-quality cells are removed from the raw sample and an improvement in % DFI is observed. However, % DFI of the DGC+SU outcome mainly depends on the raw % DFI, and improvement, in this case, is limited to the initial quality of the processed sample. For a high-quality sample (high concentration of motile sperm and % DFI below 10%), the DGC+SU method performs well and can isolate a subpopulation of sperm with less than 1% DFI. By decreasing the quality of the raw sample, the DFI % of selected sperm using DGC+SU increases, which shows its limitation in sperm selection from poor-quality semen samples. However, selected sperm using the sperm selection device showed a significantly lower ($p<0.001$) % DFI (less than 5%) than that of raw sample for all patient samples. Even for a highly fragmented sample (51.4% DFI and 10.8 million/mL motile sperm concentration), the sperm selection device outcome had 4.1% DFI. In low-quality patient samples, compared to the DGC+SU, a significant improvement ($p<0.001$) in the % DFI is observed for the sperm selection device outcome (FIG. 20, panel A).

Figure 21:
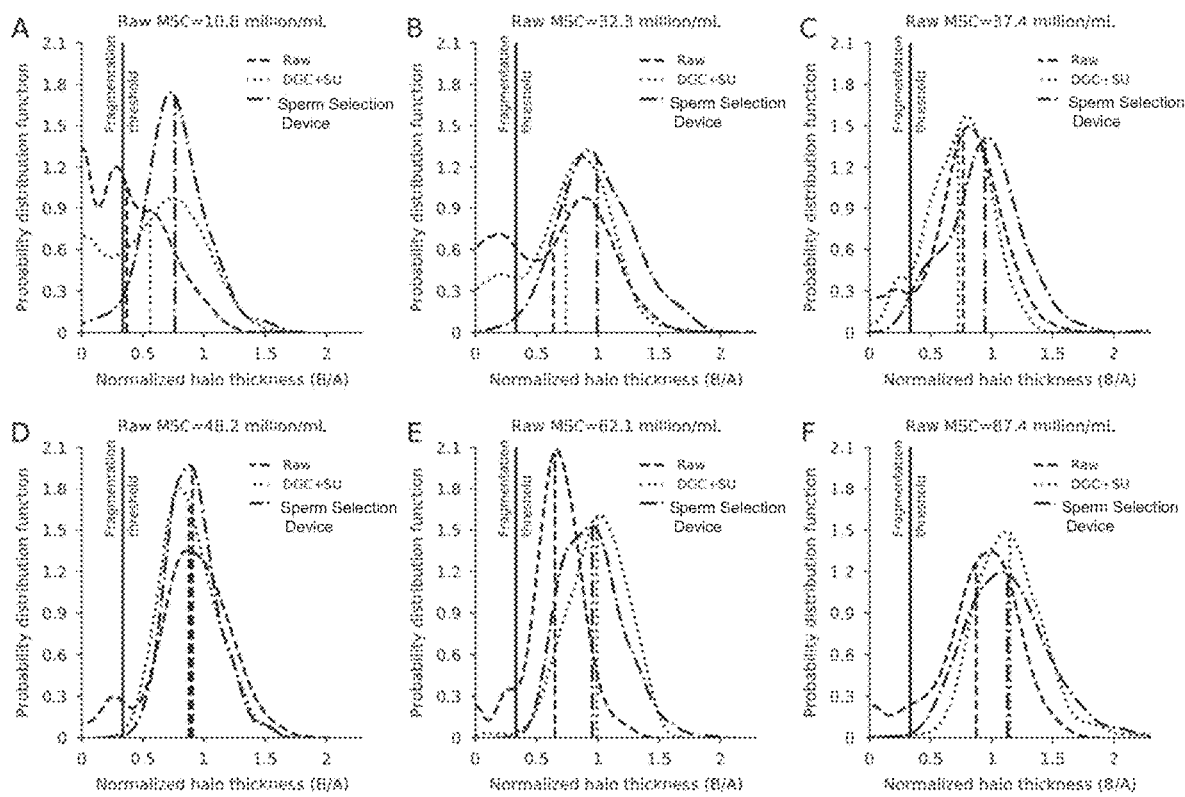
FIG. 21 shows the estimated probability distribution function of normalized DNA halo thickness of sperm selected from patient samples. The fragmentation threshold defined by the SCD kit (B/A<=1/3) is demonstrated as a solid vertical line. The vertical dashed lines represent the average B/A value of the correspondent sample. The motile sperm concentration (MSC) of each raw patient sample is mentioned in the title of each panel.
Figure 22:
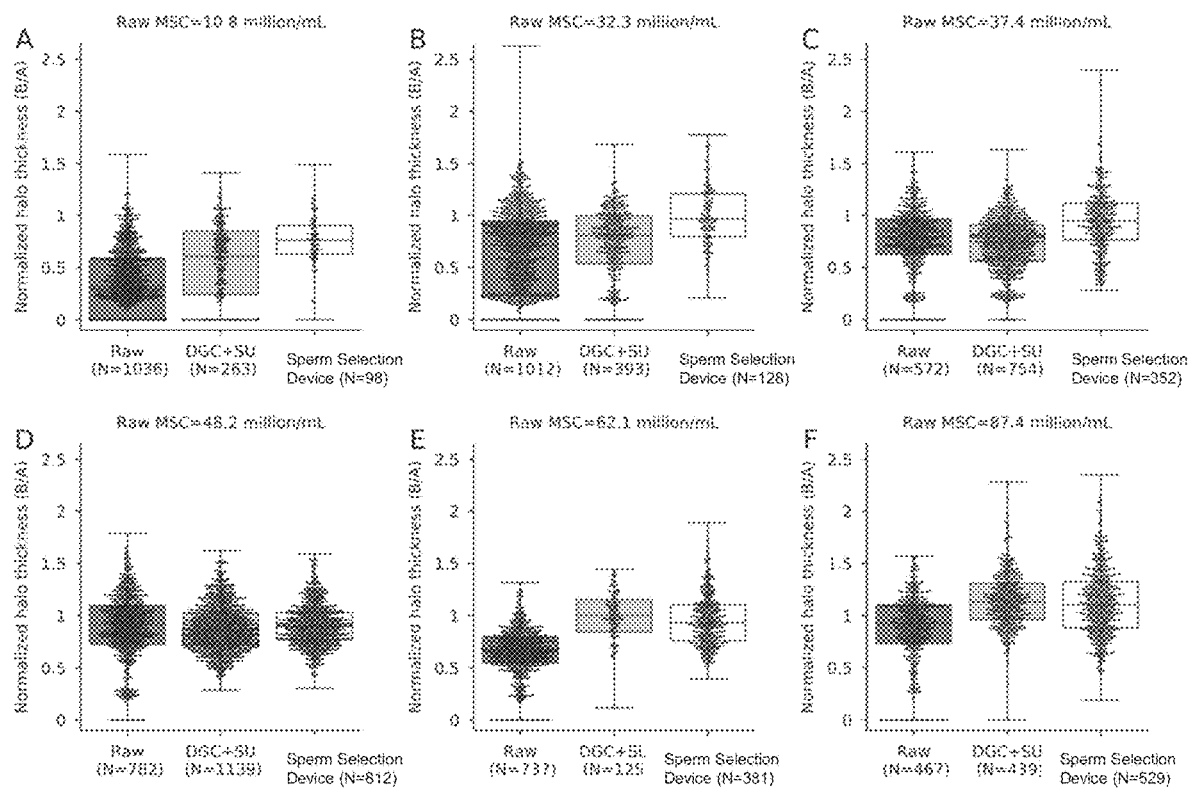
FIG. 22 shows SCD assay results for the side-by-side clinical testing. Box plot demonstrates the first quartile, median, and third quartile values as three horizontal lines of the box. The whiskers show the lowest and the largest data points. The motile sperm concentration (MSC) of each raw patient sample is mentioned in the title of each panel.

The B/A distribution of sperm samples (FIG. 21) is similar to what was observed in the donor samples results (FIG. 18, panels A, D, and G), the proportion of sperm with very high quality (large halo, B/A>1) is increased in the sperm selection device outcome. Having lower % DFI and a higher concentration of sperm with high DNA integrity results in a statistically significant ($p<0.001$) improvement in B/A average value compared to that raw sample (FIG. 20, panel B). For raw samples with normal parameters (low % DFI and high motile sperm concentration), the sperm selection device performed as well as the clinical method (DGC+SU). However, by decreasing the quality of the raw sample, the DNA quality (average B/A) of selected sperm by the DGC+SU method is reduced. In these cases, the sperm selection device outperforms DGC+SU and isolates a sperm subpopulation with much higher quality (significantly higher average B/A and lower % DFI) (FIG. 20, panels A and B). The estimated probability distribution function of data and box and swarm plots of all results are provided in FIGS. 21 and 22.

Up to a 37.5% improvement was achieved by using the sperm selection device compared to DGC+SU, (FIG. 20, panel C). For the first four samples with lower motile sperm concentration, the improvement was statistically significant ($p<0.001$ for the first three samples and $p<0.005$ for the fourth one). There was no significant difference between the sperm selection device and the DGC+SU outcome for the two other samples.

Figure 23:
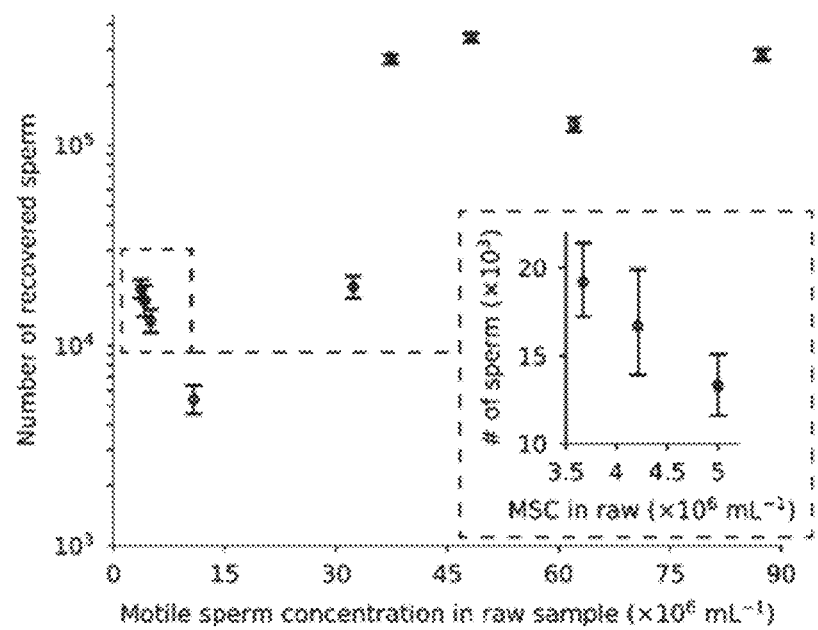
FIG. 23 shows efficiency for a sperm selection device. Number of retrieved sperm cells from the sperm selection device after selection experiments with donor and patient samples vs the initial concentration of motile sperm in the raw sample.

The number of recovered sperm from the device as a function of MSC in the raw sample is shown in FIG. 23. The results demonstrate a positive correlation between the number of sperm recovered from the sperm selection device and MSC in the raw sample. The average sperm recovery rate (percentage of recovered sperm from the raw semen) of the sperm selection device was ~0.17%, with the minimum and maximum number of retrieved cells from the device as ~5,400 ($10.8 \times 10^6$ raw sample MSC) and ~345,000 ($48.2 \times 10^6$ raw sample MSC), respectively. As the sperm selection process is based on the motility of sperm, the number of recovered sperm generally increases with motile sperm concentration. As the sperm selection device integrates thousands of sperm selection microchannels that access 1 mL of semen sample with a very high contact area, the sperm selection device can provide a high yield. A raw semen sample contains millions of live and dead sperm having a very wide range of quality. A highly selective sperm selection approach can isolate a very small proportion of sperm with very high quality. The average sperm recovery rate of the sperm selection device was 0.17%. The minimum and maximum number of retrieved sperm was about 5,400 and 345,000, respectively, which is sufficient for the downstream clinical processes, intracytoplasmic injection (ICSI) and droplet-based in-vitro fertilization (IVF). In ICSI, a single sperm is needed to be injected in each egg. A high concentration of very high-quality sperm can also be sufficient for the droplet-based IVF. Even for a poor-quality semen sample, the sperm selection device can provide a sufficient quantity of high-quality sperm candidates to meet current clinical workflow requirements.

We claim:

1. A device for selecting sperm, comprising:
    a stack of a plurality of layers of a material, the stack having an inlet end and an outlet end; and
    a core, wherein the material is wrapped around the core to form the stack;
    wherein each layer of the material comprises a plurality of sperm selection microchannels, wherein each sperm selection microchannel has a respective microchannel inlet at the inlet end of the stack and extends to a respective microchannel outlet at the outlet end of the stack.

2. The device of claim 1, wherein the stack comprises between 50 and 100,000 of the sperm selection microchannels.

3. The device of claim 1, wherein the stack comprises between 6,500 and 100,000 of the sperm selection microchannels.

4. The device of claim 1, wherein the core is a cylindrical rod.

5. The device of claim 1, wherein the core is conical and tapers in cross sectional area going from the inlet end towards the outlet end.

6. The device of claim 1, further comprising a sperm collection reservoir at the outlet end.

7. The device of claim 6, wherein an outermost layer of the material forms the sperm collection reservoir.

8. The device of claim 1, further comprising an inlet reservoir adjacent the inlet end.

9. The device of claim 1, wherein the inlet end is stepped.

10. The device of claim 1, wherein
    the device further comprises a second stack of a second plurality of layers of the material;
    wherein the second stack has a second inlet end and a second outlet end; and
    wherein the device further comprises a sperm collection reservoir between the first stack and the second stack and adjacent the outlet end and the second outlet end.

11. The device of claim 1, wherein at least some of the sperm selection microchannels comprise a respective corner.

12. The device of claim 1, wherein at least some of the sperm selection channels are triangular or trapezoidal in cross-section.

13. The device of claim 1, wherein a first set of the sperm selection channels are triangular in cross-section, and second set of the sperm selection channels are trapezoidal in cross-section.

14. The device of claim 1, wherein the material is a polyethylene terephthalate film.

15. A kit of parts for selecting sperm, comprising:
- a device comprising a stack of a plurality of layers of a material and a core, wherein the material is wrapped around the core to form the stack, wherein the stack has an inlet end and an outlet end, wherein each layer of the material comprises a plurality of sperm selection microchannels, and each sperm selection microchannel has a respective microchannel inlet at the inlet end of the stack and extends to a respective microchannel outlet at the outlet end of the stack; and
- a vessel having an interior volume;
- wherein the device is connectable to the vessel to position the microchannel inlets in the interior volume, and wherein at least one of the device and the vessel provides a sperm collection reservoir in fluid communication with the microchannel outlets.

16. A method for fabricating a sperm selection device, comprising:
- a. creating a plurality of sperm selection microchannels in a material, wherein each sperm selection microchannel has a microchannel inlet and a microchannel outlet;
- b. arranging the material into a stack of a plurality of layers of the material by wrapping the material around a core, so that the microchannel inlets are at an inlet end of the stack and the microchannel outlets are at an outlet end of the stack.

17. The method of claim 16, wherein step a. comprises creating the sperm selection microchannels using laser ablation, cutting plotter engraving, cutting plotter scratching, soft lithography, injection molding, micromilling, micromachining, 3D-printing, xurography, wet etching, dry etching, powder blasting, sand blasting, polymer casting, sawing, stamping, and/or hot embossing.

18. The method of claim 16 wherein step a. comprises creating at least 6,500 of the sperm selection microchannels.

\* \* \* \* \*